United States Patent [19]

Zeilstra et al.

[11]  4,323,495
[45]  Apr. 6, 1982

[54] NOVEL BRANCHED-CHAIN MONOALCOHOLS AND DERIVATIVES THEREOF, LUBRICANT COMPOSITIONS FOR POLYMERS AND WAX COMPOSITIONS IN WHICH THESE NOVEL PRODUCTS ARE INCORPORATED

[75] Inventors: Jacobus J. Zeilstra, Wijnbergen; Willem J. de Klein, Dieren; Joannes D. Bik, Eerbeek, all of Netherlands

[73] Assignee: Akzona Incorporated, Asheville, N.C.

[21] Appl. No.: 88,614

[22] Filed: Oct. 26, 1979

[30] Foreign Application Priority Data

Oct. 26, 1978 [NL] Netherlands .......................... 7810669

[51] Int. Cl.$^3$ ............................................. C08L 91/00
[52] U.S. Cl. ............................... 524/156; 106/287.26; 260/410.9 R; 260/457; 260/464; 260/465 R; 260/465.1; 260/465 H; 560/1; 560/8; 560/129; 560/190; 568/613; 568/840; 524/198; 524/295; 524/296; 524/298; 524/314; 524/376; 524/385; 524/569
[58] Field of Search .................... 260/457, 464, 465 R, 260/465.1, 465 H, 42.49, 33.4 PQ, 410.9 R, 31.2 R, 33.2 R, 32.4, 28.5 D; 560/1, 8, 129, 190; 568/613, 840; 106/287.26

[56] References Cited

FOREIGN PATENT DOCUMENTS 2613996 10/1976 Fed. Rep. of Germany .
1547857  6/1979 United Kingdom .

*Primary Examiner*—Melvyn I. Marquis
*Attorney, Agent, or Firm*—Francis W. Young; Daniel N. Christus

[57] ABSTRACT

Novel branched-chain monoalcohols and derivatives thereof are disclosed. Such derivatives are selected from the group consisting of
(a) esters of aromatic, aliphatic or cycloaliphatic acids having at least 2 carbon atoms and 1, 2 or 3 carboxyl groups;
(b) urethanes of aromatic, aliphatic or cycloaliphatic isocyanates;
(c) monoethers of polyalkylene oxide glycols having 2 to 50 alkylene oxide units each containing 2 or 3 carbon atoms and the alkylpolyoxyalkylene sulfates derived therefrom;
(d) sulfates.

The branched-chain monoalcohols are obtained by reduction of branched-chain monocarboxylic acids or esters thereof. Said acids are telomeric acids obtained by the free radical addition of 1 mole of acetic anhydride to at least three moles of hexene and/or higher olefins containing up to 30 or more carbon atoms ($C_{30+}$) in the presence of a trivalent manganese compound. The products of this invention are suitable for use in engine lubricating oils, lubricant compositions for polymers and wax compositions.

15 Claims, No Drawings

NOVEL BRANCHED-CHAIN MONOALCOHOLS AND DERIVATIVES THEREOF, LUBRICANT COMPOSITIONS FOR POLYMERS AND WAX COMPOSITIONS IN WHICH THESE NOVEL PRODUCTS ARE INCORPORATED

The invention relates to novel branched monoalcohols having at least 20 carbon atoms, and the derivatives thereof selected from the group consisting of
(a) esters of aromatic, aliphatic or cycloaliphatic acids having at least 2 carbon atoms and 1, 2 or 3 carboxyl groups;
(b) urethanes of aromatic, aliphatic or cycloaliphatic isocyanates;
(c) monoethers of polyalkylene oxide glycols having 2 to 50 alkylene oxide units each containing 2 or 3 carbon atoms and the alkylpolyoxyalkylene sulfates derived therefrom;
(d) sulfates, to lubricant compositions for polymers which are entirely or partly composed of one or more of these alcohols and/or derivatives thereof, and to wax compositions for entirely or partly replacing carnauba or montan wax and substantially consisting of one or more of these alcohols and/or derivatives thereof. Branched-chain monoalcohols and the esters derived therefrom are known from, inter alia, U.S. Pat. No. 2,862,013. The alcohols are obtained by Guerbet condensation of lower alcohols. A drawback to this method of preparation is that it is relatively costly.

Moreover, the alcohols obtained have not more than 24 to 28 carbon atoms.

Also the German Patent Specification No. 2 613 996 describes a process for the preparation of branched-chain alcohols and the esters built up therefrom. According to the general formula alcohols having not more than 18 carbon atoms are obtained. The examples merely include the preparation of 2,4-diethyloctanol, i.e. an alcohol having 12 carbon atoms.

Applicant has found that the preparation of branched-chain alcohols and the esters derived therefrom having a product composition which entirely differs from the one described in the above-mentioned patent specifications leads to products having remarkably better properties for quite a number of uses.

The present invention provides a novel class of branched-chain monoalcohols and derivatives therefrom.

The invention consists in that the alcohols, from which also the derivatives of the known type mentioned in the opening paragraph are derived, conform to the formula:

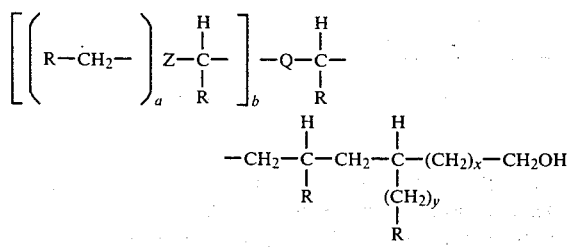

where
$x=0$, if $y=2$ or $x=2$, if $y=0$
$R=CH_3(CH_2)_n$, where n represents an integer from 3 to 42; b is 0 or 1, where if $b=0$, Q represents a hydrogen atom, and if $b=1$, Q represents a $CH_2$-group, and $a=0$ or 1, where if $a=0$, Z represents a hydrogen atom, and if $a=1$, Z represents a $CH_2$-group.

It has been found that in the preparation for a large number of uses of the derivatives it is preferred that they should be derived from alcohols where $n=3$ to 17. These derivatives find application as lubricant for polymers and in the preparation of surface active compounds and engine lubricants. Particularly with the use of the alcohols as such, for instance as lubricant in resin compositions for polymers and in wax compositions, it is preferred to employ branched-chain alcohols of the above formula where n represents an integer of from 17 to 42.

For the preparation of the novel esters according to the present invention it is preferred to start from an aliphatic acid having 1 to 30 carbon atoms. For most uses, as in lubricant compositions for polymers, the object will be to obtain good processing properties in combination with minimum volatility. According to the invention the branched-chain alcohols are therefore often esterified with a di- or a tricarboxylic acid.

Particularly the esters derived from acetylene dicarboxylic acid, fumaric acid, maleic acid or adipic acid are found to lead to products which are excellently suitable for entirely or partly replacing carnauba wax.

Representative examples of monocarboxylic acids to be used according to the invention include acetic acid, propionic acid, butyric acid, cyclohexyl carboxylic acid, valeric acid, pivalic acid, oleic acid and lauric acid.

Representative examples of dicarboxylic acids to be used according to the invention include sebacic acid, cyclohexane-1,4-dicarboxylic acid, adipic acid, glutaric acid, succinic acid, oxalic acid, azelaic acid, furan 3,4-dicarboxylic acid, terephthalic acid and isophthalic acid.

An example of an acid having three carboxyl groups is citric acid. The acid number of these esters is preferably lower than 30 and the hydroxyl number lower than 40. The esterification reaction may be carried out in the usual manner. The reaction mixture is heated in the presence or not of a catalyst at a temperature in the range of 100° to 300° C. and the water evolved in the reaction is carried off. The esterification is usually carried out at a temperature in the range of 140° to 280° C.

Optionally, use may be made of an esterification catalyst. This may be an acid such as sulphuric acid, phosphoric acid, alkylsulphonic acids and arylsulphonic acids such as p-toluene sulphonic acid and methane sulphonic acid, and a variety of metal compounds such as dibutyl tin oxide, tetrabutyl titanate, zinc acetate, stanno-oxalate, iron oxide, ferristearate, manganostearate, cobalt (II) stearate and manganoacetate.

The catalyst is usually employed in an amount of 0.1 to 1% by weight, based on the reaction mixture. Optionally, use may be made of an inert thinner such as benzene, toluene or xylene, which together with water forms an azeotrope.

In the process use is generally made of stoichiometric amounts of acid and alcohol. Esterification may take place at atmospheric pressure, but may be carried out at reduced pressure (2-50 mm Hg). Under such conditions water and other volatile constituents can readily be removed upon completion of the reaction. The resulting esters are as a rule directly suitable for one or more of the above-mentioned uses. Under some circumstances, however, it may be advisable also to apply a purification step, for instance by treating the compositions with bleaching earth, ozone, peroxide, hypochlorite or some other suitable bleaching agent. The preparation also may include a treatment with active carbon.

The isocyanates to be used in the preparation of the urethanes of the present invention may be of an aliphatic, cycloaliphatic or aromatic character. If few or no coloured products are desired, then it is preferred to use aliphatic isocyanates. Preference is further given to isocyanates of the general formula A-$R_1$—NCO, where $R_1$ represents a (cyclo) aliphatic hydrocarbon having at least 6 carbon atoms, a phenyl group or naphthyl group, which groups may be substituted or not with one or more lower alkyl groups having 1 to 8, and preferably 1 to 6 carbon atoms, lower alkoxy groups having 1 to 8, and preferably 1 to 6 carbon atoms, aryl, for instance phenyl, and halogen such as chlorine or bromine, and A represents a —NCO group, or a —$R_2$—($CH_2$—$R_3$—NCO$)_n R_4$ NCO group where $R_2$ has the meaning of a simple bond or an aliphatic hydrocarbon group having 1 to 4 carbon atoms, n is equal to 0 or higher, and $R_3$ and $R_4$ may be the same or different and may or may not have the same meaning as $R_1$.

As examples of suitable monoisocyanates may be mentioned ethyl isocyanate, hexyl isocyanate, 2-ethylhexyl isocyanate, butyl isocyanate, stearyl isocyanate. As examples of diisocyanates which can be defined by the formula OCNRNCO, where R represents a divalent aliphatic, alicyclic or aromatic group, may be mentioned:
hexamethylene diisocyanate;
dimethyl hexamethylene diisocyanate;
trimethyl hexamethylene diisocyanate;
metaxylene diisocyanate;
paraxylene diisocyanate;
tetramethylene diisocyanate.
In the case where R represents an aromatic group, it may be substituted with a halogen, a lower alkyl or a lower alkoxy group.

As examples of such diisocyanates may be mentioned:
1-chloro-2,4-phenylene diisocyanate;
2,4-toluene diisocyanate;
a mixture of 2,4-toluene diisocyanate and 2,6-toluene diisocyanate;
tetramethylphenylene diisocyanate;
diphenylmethane-4,4'-diisocyanate;
metaphenylene diisocyanate;
paraphenylene diisocyanate;
1,5-naphthalene diisocyanate;
biphenyl-4,4'-diisocyanate;
diphenylmethane-4,4'-diisocyanate;

4,4'-isopropylidene diphenylisocyanate;
benzophenone-4,4'-diisocyanate;
diphenylether diisocyanate or diphenylsulphide diisocyanate;
3,3'-dimethyldiphenyl-4,4'-diisocyanate;
3,3'-dimethoxydiphenyl-4,4'-diisocyanate;
3,3'-dichlorodiphenyl-4,4'-diisocyanate;
benzofuran-2,7-diisocyanate.

Examples of diisocyanates having an cycloaliphatic group include isophoron diisocyanate, dicyclohexyl methane diisocyanate and 1,4-cyclohexane diisocyanate.

The temperature at which the reaction takes place between the alcohol and the isocyanate should be established experimentally. It will generally be in the range of 60° to 200° C.

The reaction of the alcohols according to the invention with the isocyanate compounds is carried out in a manner known in itself. The conversion may be carried out in the melt or in an inert solvent. Examples of suitable solvents include methylene chloride, carbon tetrachloride, benzene, chlorobenzene, methylethyl ketone, tetrahydrofuran, dioxane, glycolmonomethylether acetate, glycol formal, dichlorobenzene, trichlorobenzene, nitrobenzene, benzoic methyl ester or acetophenone. If the conversion is carried out in solvents, especially relatively low boiling ones, such as methylene chloride, the solvents may be distilled off as the reaction progresses.

The preparation of the monoethers of the present invention is usually carried out in two steps: (a) addition of ethylene oxide and/or propylene oxide to the alcohol to form a monoadduct, followed by (b) subsequent addition(s) of ethylene oxide and/or propylene oxide in a polymerization reaction. The alkoxylation reaction is catalysed by bases such as NaOH, NaOCH$_3$ or KOH in an amount of about 0,005 to 0,05 mole of base per mole of alcohol. The reaction temperature is generally chosen between 100° and 200° C. The alkoxylation is generally carried out as a batch reaction. After the reaction is complete, the catalyst is neutralized and the product is discharged to storage or packaged. The alkylpolyoxyalkylene sulfates are prepared with amidosulfuric acid as the sulfating agent. This sulfation technique leads directly to the formation of the ammonium salt. Sodium salts can be prepared by adding caustic soda and driving off the ammonia with heat. Though the ammonium and/or sodium ion can be replaced by an innumerous number of different cations, preference is given to a cation selected from the group of ammonium, sodium, potassium, magnesium, diethanolamine and triethanolamine. The alcohols of the present invention may also be sulfated directly in the same manner as described hereabove for the sulfation of alkylpolyoxyalkylene oxide glycol with the aid of amidosulfuric acid. Preference is given for the same cations as is the case for the alkylpolyalkylene sulfates.

The alcohols of the first-mentioned formula can be obtained by reduction in a manner known in itself of an acid, or of an ester thereof having the formula

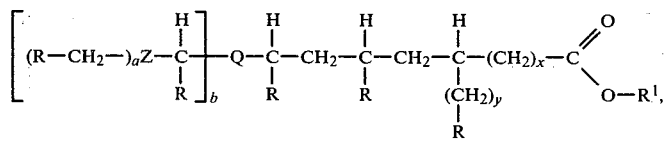

where R, Z, Q, a, b, x and y have the above-indicated meanings and $R^1$ represents a hydrogen atom (for the acid), or a preferably lower alkyl group having 1 to 4 carbon atoms.

Reduction with hydrogen may for instance be carried out in the presence of a copper chromite catalyst at a pressure of 170 to 230 atmospheres and a temperature of 100° to 320° C.

The starting product required for the preparation of the present alcohols is obtained by esterification of the corresponding acid with a lower aliphatic alcohol or the acid itself.

The preparation of the acid is effected by reacting an α-olefin having 6 to 45 carbon atoms with acetic anhydride at a temperature in the range of 100° to 140° C. in the presence of a catalytic amount of an at least trivalent manganese compound. The α-olefin may consist of a pure olefin fraction, such as 1-octene, or of a mixture of α-olefins having 6 to 45 carbon atoms. If use is made of a mixture of α-olefins the number for n in each separate R-radical may, independently of the other R-radicals in the structural formula of the acid and of the alcohol to be prepared therefrom, assume any value equal to the number of carbon atoms minus two of an α-olefin present in the mixture. The most favourable results are generally obtained at a reaction temperature in the range of 115° to 125° C. in the presence of manganic acetate as initiator. To prevent oxidation of the substrate the concentration of the manganic acetate is preferably chosen between $10^{-3}$ and $10^{-10}$ moles per liter.

The concentration of the olefin fraction is dependent on the desired percentage of branched-chain monocarboxylic acids in the reaction product.

If use is made of an olefin fraction having not more than 12 carbon atoms, preference is usually given to a relatively high percentage of branched-chain acids. If, however, use is made of an olefin fraction having 20 to 45 carbon atoms, then there is found to be a strong preference to a mixture of monocarboxylic acids which contains at least 70% by weight of the addition product of 1 mole of olefin to 1 mole of acetic acid. In all cases the reaction conditions will be so chosen that ultimately at least 10% by weight of the branched-chain alcohols conforms to the first-mentioned structural formula. For the preparation of branched-chain monocarboxylic acids from which the esters according to the above formula are derived, the molar ratio of converted olefin to manganic acetate is at least 4. It has been found that under these last-mentioned conditions the composition in weight % of the mixture of telomeric acids and, hence, of the alcohols prepared therefrom is for $n<17$ only dependent on the molar ratio of α-olefin to manganic acetate and the concentration of the α-olefin during the reaction.

With a monocarboxylic acid obtained by reacting one α-olefin with acetic acid being indicated by $R_1$, a monocarboxylic acid obtained by reaction with two α-olefins by $R_2$, a monocarboxylic acid obtained by reaction with three α-olefins by $R_3$, etc., then, for instance, the following weight distributions were obtained respectively before and after removal of the $R_1$-fraction.

|  | before distillation | after distillation |
| --- | --- | --- |
|  | wt % | wt % |
| $R_1$ | 30,7 | 0,3 |
| $R_2$ | 20,4 | 19,8 |
| $R_3$ | 21,4 | 33,6 |
| $R_4$ | 13,0 | 21,5 |
| $R_5$ | 9,4 | 15,9 |
| $R \geq 6$ | 5,1 | 8,8 |

The structural formulae of $R_3$, $R_4$ and $R_5$ all conform to the first-mentioned formula. $R_1$ is an unbranched acid of the formula $R(CH_2)_3 COOH$ and, if $n=3$ to 9, it is preferably removed from the reaction mixture after esterification of the mixture with a lower aliphatic monofunctional alcohol.

The fraction of $R_2$ is formed by two acids of the formula:

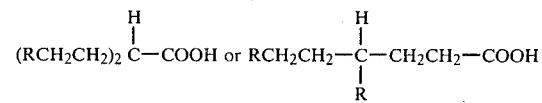

For a man skilled in the art it is obvious that, especially if use is made of an olefin fraction having 30 or more carbon atoms, it is not possible in actual practice to separate the linear acids and the acids having a very high molecular weight and a high degree of telomerization and the derived esters and alcohols.

The following is a typical example of a weight distribution of the monocarboxylic acids obtained under said conditions and, hence, of the alcohols prepared therefrom.

| degree of telomerization | wt % |
| --- | --- |
| m = 1 | 78,0 |
| m = 2 | 6,3 |
| m = 3 | 6,5 |
| m = 4 | 4,0 |
| m = 5 | 3,1 |
| m ≧ 6 | 2,0 |

It has been found that as far as the above-mentioned field of application of polymers, wax compositions, etc., is concerned the use of mixtures of alcohols derived from these branched-chain and straight-chain carboxylic acids and the derivatives thereof lead to compositions having unexpectedly favourable properties, which remarkably favourably compare with the known compositions, which only contain straight-chain alcohols or the derivatives thereof.

The commercially available olefin fractions having 20 to 45 carbon atoms are found to contain 60 to 80% by weight of α-olefins and for the rest predominantly consist of vinylidene compounds.

The resulting alcohols are γ-branched monoalcohols, with the alcohol having the formula

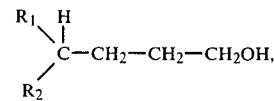

where $R_1$ and $R_2$ represent linear alkyl groups which together have the same number of carbon atoms as the group R.

Separation of these vinylidene groups-containing fractions from the α-olefins would give rise to so many technological problems that it must be considered impracticable for economic reasons. It has been found, however, that for most uses products having exceptionally good properties are obtained if besides the branched-chain alcohols having the above formulae or the derivatives thereof there is present an amount of 40 to 60 percent by weight of the alcohol fraction or of the derivatives thereof which consists of or is derived from linear aliphatic monoalcohols, with the alcohol having the formula $R\ CH_2CH_2CH_2CH_2OH$, where R represents a $CH_3(CH_2)_n$ group, with n being an integer of from 17 to 42.

The invention also relates to a resin composition having improved internal and external lubricating properties, comprising a polymer or copolymer of vinyl chloride and 0,1 to 5% by weight, calculated on the polymer, of an alcohol or a derivative thereof according to the opening paragraph, characterized in that at least 40 percent by weight of the alcohol present as such, or at least 40 percent by weight of the alcohol from which the derivatives are derived, have a branched-chain structure, and at least 10 percent by weight thereof conform to the above first-mentioned formula.

It has been found that the quality of the resin compositions is not detrimentally influenced if besides the branched-chain alcohols and/or the derivatives thereof, with the alcohol having the above first-mentioned formula, there is still present an alcohol and/or a derivative thereof with the alcohol having the formula:

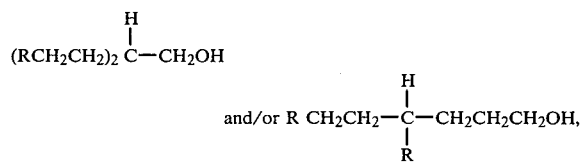

where R has the meaning given for it with the first-mentioned formula. As indicated above, the commercially available olefin fractions having 24 to 50 or more carbon atoms in considerable part consist of vinylidene compounds.

These cannot be removed or only with very great difficulty. It has been found, however, that resin compositions having excellent processing properties can be obtained if besides the branched-chain alcohols and/or the derivatives thereof with the alcohols having the first-mentioned formula and the two last-mentioned ones, there is present an amount of 40 to 60 percent by weight of linear aliphatic monoalcohols and/or derivatives thereof, with the alcohol having the formula $R(CH_2)_3CH_2OH$, where R has the meaning given for it with the first-mentioned formula, and about 30 to 40 percent by weight of γ-branched primary alcohols and/or the derivatives thereof, with the alcohol having the formula

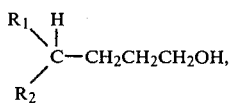

where $R_1$ and $R_2$ represent linear alkyl groups which together have the same number of carbon atoms as the group R.

By polyvinyl chloride and copolymers of polyvinylchloride are to be understood here all possible types of homopolymers of vinyl chloride, and post-chlorinated polyvinyl chloride, and also copolymers whose most important constituent is vinyl chloride, and a small proportion of other copolymerizable monomers, such as copolymers of vinyl chloride and vinyl acetate, copolymers of vinyl chloride and vinylidene chloride, copolymers of vinyl chloride and acrylonitrile, copolymers of vinyl chloride and maleic or fumaric esters and copolymers of vinyl chloride and styrene, and also mixtures containing a high percentage of polyvinyl chloride resin and a small percentage of some other synthetic resin, such as chlorinated polyethylene, copolymers of acrylonitrile, butadiene and styrene.

The lubricants may be incorporated into the polyvinyl chloride or copolymers thereof in the usual manner. This may be done by mixing on a roll or in a mixer of the Banbury type.

Alternatively, the lubricant may be dissolved or dispersed in some appropriate solvent.

The lubricant may be added along with other composition ingredients such as stabilizers, fillers and plasticizers, or in a separate step. The physical properties of the formulated resin composition may be considerably varied by changing the amount and the nature of the constituents to be incorporated therein without detracting from the lubricating properties of the present lubricants.

For a man skilled in the art it will generally not be difficult to find the most suitable percentage for obtaining an optimum effect for each use envisaged. In a number of cases it will be posible for the alcohols or derivatives according to the present invention to be used as such, i.e. without admixing other known polymer and/or engine lubricating agents, but generally it will be preferred that other products should be admixed in order to obtain more favourable physical and/or chemical properties.

The invention further relates to a wax composition for entirely or partly replacing carnauba wax or montan wax and substantially consisting of one or more alcohols and/or derivatives thereof characterized in that at least 40 percent by weight of the alcohol present as such, or at least 40 percent by weight of the alcohol from which the derivatives are derived, is branched, and at least 10 percent by weight thereof conforms to the above first-mentioned formula.

It has been found that the quality of the wax compositions is not detrimentally influenced if besides the branched-chain alcohols or the derivatives thereof, with the alcohol having the above first-mentioned formula, there is present an alcohol or derivative thereof, with the alcohol having the formula

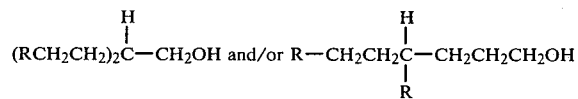

where R has the meaning given for it with the first-mentioned formula.

As mentioned above, the commercially available olefin fractions having 24 to 50 or more carbon atoms in considerable part consist of vinylidene compounds. They cannot be removed or only with great difficulty. It has been found, however, that wax compositions having excellent properties can be obtained if besides the branched-chain alcohols or the derivatives thereof, with the alcohols having the first-mentioned formula and the two last-mentioned ones, there is present an amount of 40 to 60 percent by weight of linear aliphatic mono alcohols or derivatives thereof, with the alcohol having the formula $R(CH_2)_3 CH_2OH$, where R has the meaning given for it with the first-mentioned formula, and about 30 to 40 percent by weight of γ-branched primary alcohols or the derivatives thereof, with the alcohol having the formula:

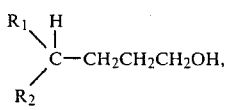

where $R_1$ and $R_2$ represent linear alkyl groups which together have the same number of carbon atoms as the group R.

The invention is further described in, but not limited by the following examples.

EXAMPLE I

For the preparation of branched-chain acids use was made of a commercially available starting mixture of olefins consisting of about 22% by weight of olefins having not more than 28 carbon atoms and about 78% by weight of olefins having at least 30 carbon atoms ($C_{30}$+olefins), about 66% by weight of the olefins being α-olefins. The remaining olefin compounds were vinylidene compounds. The reaction was carried out in a stirred (700 r.p.m.) reactor provided with 8 baffles and equipped with a stirrer having 6 diametrically opposed blades. Into this reaction vessel there were charged 12,5 liters (132 moles) of acetic anhydride. The liquid was heated to 120° C. while nitrogen was slowly passed through to remove the oxygen present in it. With the liquid being kept at 120° C., first of all the $C_{30+}$ olefin mixture was added. Of this mixture in all 1175 g (2,5 moles) were added over a period of 210 minutes. 12 minutes after a start had been made with adding olefin a slurry of 0,625 moles Mn (III) acetate in 2,5 l acetic anhydride was added over a period of 216 minutes (so for a period of 18 minutes after the last of the olefin had been added addition of Mn (III) acetate was continued to ensure complete conversion of the olefin).

The mixture was subsequently filtered to remove the Mn(II) acetate that had formed. Next, acetic anhydride and the acetic acid formed were removed by distillation. To the residue there were added 2,5 l acetic acid and 0,3 l water. With vigorous stirring the mixture was boiled with refluxing to hydrolyse the obtained anhydrides. Finally, the water-acetic acid layer was separated off, the product washed 3 times with hot water and dried.

The resulting mixture of straight-chain and branched-chain acids had an acid number of 86.

Of the acid thus obtained 1025 g were transferred to an autoclave which was heated to about 100° C. To the molten acid 51,25 g of a barium-promoted copperchromite catalyst were added, after which the system was rinsed three times with nitrogen and once with hydrogen.

Subsequently, hydrogen was fed in up to a pressure of 174 atmospheres. The temperature was then allowed to rise from 100° to 310° C. over a period of 50 minutes, after which the pressure rose to 223 atmospheres. Over a period of 23 minutes hydrogen was used up to such a degree that the pressure decreased to 178 atmospheres.

Next, the temperature was decreased to 100° C. and hydrogen fed in under a pressure of up to 174 atmospheres. The temperature was again allowed to rise over a period of 50 minutes to a value of 310° C., at which temperature a pressure of 229 atmospheres was obtained. Afterwards no longer any decrease in pressure was observed, so that the reaction could be considered completed. After filtration of the reaction mixture a light coloured product was obtained having a residual acid number of <5 and a hydroxyl number of 81.

EXAMPLE II

In this example use was made of a starting mixture of telomeric acids derived from n-decene. This mixture had been obtained by removing the lower telomeric fraction and was composed as follows:

|       | wt % |
|-------|------|
| n = 1 | <5   |
| n = 2 | 30   |
| n = 3 | 35   |
| n = 4 | 15   |
| n = 5 | 10   |
| n = 6 | 5    |

Using the same procedure as indicated in Example I 817 g of this mixture (acid number 104) were mixed with 40,85 g of barium-promoted copper chromite (5% by weight, calculated on the substrate).

After 3×rinsing with nitrogen and 1×with hydrogen at a pressure of 20 atmospheres and a temperature of 25° C. hydrogen was fed in up to a pressure of 179 atmospheres. Subsequently, over a period of 55 minutes, the temperature was increased to 310° C. After 55 minutes at 310° C. the pressure had dropped from 247 atmospheres to 199 atmospheres. The system was cooled to 90° C., and hydrogen was fed in up to a pressure of 176 atmospheres, after which the temperature was increased to 310° C. over a period of 45 minutes. When after 3 hours no longer any pressure drop was observed, the product was isolated by filtration. The residual acid number was 5 and the hydroxyl number 106.

EXAMPLE III

In this example an illustration is given of the fitness as lubricant in a polyvinyl chloride (PVC) formulation of the novel monoalcohols and the esters derived therefrom according to the present invention and a comparison is made with a few commercially available lubricants.

Product A=butane diol ester of montanic acid of which 40% is saponified with calcium.

Product B=a mixture composed of tridecyl stearate and equal parts by weight of glycerol mono-oleate and pentaerythritol adipate/oleate.

Product C=a mixture of mono-alcohols prepared from an olefin fraction having 22-26 carbon atoms.

Product D=a mixture of mono-alcohols prepared from an olefin fraction having 26 to 30 carbon atoms.

Use was made of the following test methods:
1. Brabender test for determining the rheological properties, the most important parameters being the gelation time and the melt viscosity (torque upon gelation and the torque 5 minutes after gelation).
2. High speed mill test for studying the behaviour during processing, such as calendering.

The polymer is observed for sticking to the roll (stick time) and change in colour both at elevated temperature and at high speeds.
3. Clarity. This property was determined by moulding formulated PVC mixtures into plates about 1 mm thick and subsequently visually evaluating the clarity.

Procedure

Each formulation was intensively mixed on a Papenmeier mixer. Part of the mixture was used for testing in the Brabender Plasticorder under the following conditions:

| | |
|---|---|
| temperature | 170° C. |
| speed | 30 revolutions per minute |
| sample weight | 30 g |

Another part of the mixture was thoroughly mixed on a roll mill at 160° C. until the mixture was entirely homogeneous. The required samples were cut out of a rolled sheet about 2 mm thick.

The samples were heated in an air circulation oven at 185° C., from which they were removed at 10 minute intervals, after which they were visually evaluated for change in colour. This colour change was taken as a measure of the decomposition rate of the PVC compound. The results of the experiments are combined in the following table and rated from 1 to 5, where
3 = slow gradual change;
4 = good early colour, rapid colour change;
5 = good
1 = poor
2 = fairly rapid gradual degradation.

The formulation of the polyvinyl chloride used in this example was as follows:

| | Parts by weight |
|---|---|
| PVC - suspension polymer | 100 |
| dibutyl-tin-bis-laurylmercaptan | 1,0 |
| mixture of monobutyl tin trisisooctyl-thioglycolate | |
| dibutyl tin bisisooctylthioglycolate | 1,0 |
| epoxidized soybean oil | |
| phenolic antioxidant | |
| lubricant | 0,5 |

1. Brabender test

| | lubricant (parts by weight) 0,5 gelation time (s) |
|---|---|
| type of lubricant | |
| control | 85 |
| product A | 330 |
| product B | 105 |
| product C (invention) | 70 |
| product D (invention) | 145 |
| | torque upon gelation |
| control | 650 |
| product A | 540 |
| product B | 610 |
| product C (invention) | 640 |
| product D (invention) | 620 |

2. High speed mill test

| type of lubricant | lubricant (parts by weight) 0,5 time (min.) after which polymer sticks to roll |
|---|---|
| control | 10 |
| product A | 40 |
| product B | 35 |
| product C (invention) | 20 |
| product D (invention) | 40 (no discoloration) |

The above test results show that the products according to the invention may best be considered an external lubricant. Rather surprising is that at a relatively high concentration of 0,5 parts by weight per 100 parts of polymer the clarity of the polymer was still excellent where use made of the product C.

3. Clarity and thermal stability

| type of lubricant | 0,5 clarity | 0,5 thermal stability |
|---|---|---|
| control | good | 3 |
| product A | poor | 3 |
| product B | — | 4 |
| product C (invention) | excellent | 3 |
| product D (invention) | poor | 3 |

EXAMPLE IV

In this example the test results are given for the $C_{30+}$ alcohols prepared according to Example I and the urethane of toluene diisocyanate and the acetic esters, adipic esters and $C_{30+}$ acid ester thereof in a PVC-formulation. The formulation of the PVC used was as follows:

| | parts by weight |
|---|---|
| PVC-suspension polymer | 100 |
| di($\beta$-carbobutoxyethyl)tin bisiso octylthioglycolate | 2 |
| lubricant | 0,3–1,0 |

Each formulation was intensively mixed on a Papenmeier mixer. Part of the mixture was used for testing in the Brabender Plasticorder under the following conditions:

| | |
|---|---|
| temperature | 160° C. |
| speed | 30 revolutions per minute |
| sample weight | 32,5 g |
| pressure | 5 kg |

Clarity

To determine the influence of the lubricant on the clarity of the stabilized formulations 3 mm thick sheets had been pressed at 190° C. Samples of the gelation experiments were taken 10 minutes after gelation. The transmission of these sheets was measured with a Bausch and Lomb spectrophotometer. The transmission at 690 nm was used as a measure of the clarity of the sheet.

The results of the Brabender gelation tests and clarity tests on the above-mentioned lubricants are summarized in the table below.

| lubricant | phr | Brabender gelation test | | | | | clarity of 3 mm thick pressed sheet at 690 nm % T |
|---|---|---|---|---|---|---|---|
| | | gelation time (min.) | fusion torque (m grams) | torque 10 min. after gelation (m grams) | temp. at fusion (°C.) | temp. after 10 min. (°C.) | |
| $C_{30+}$ alcohols | 0,3 | 5,1 | 2600 | 2850 | 163 | 170 | 73 |
| | 0,5 | 11,6 | 2550 | 2800 | 167 | 171 | 40 |
| acetic acid esters of $C_{30+}$ alcohols | 0,3 | 5,1 | 2575 | 2850 | 163 | 170 | 76 |
| | 0,5 | 9,6 | 2575 | 2850 | 164 | 171 | 50 |
| adipic acid diesters of $C_{30+}$ alcohols | 0,3 | 6,7 | 2550 | 2850 | 163 | 171 | 47 |
| | 0,5 | 25,3 | 2400 | 2700 | 163 | 170 | 23 |
| $C_{30+}$ acid esters of $C_{30+}$ alcohols | 0,3 | 4,2 | 2500 | 2850 | 162 | 170 | 76 |
| | 0,5 | 8,8 | 2500 | 2850 | 163 | 170 | 54 |
| diurethane of toluene diisocyanate and $C_{30+}$ alcohol | 0,3 | 6,3 | 2550 | 2875 | 163 | 170 | 75 |
| | 0,5 | 10,1 | 2575 | 2800 | 165 | 170 | 44 |
| control | — | 1,2 | 2700 | 2850 | 156 | 171 | 85 |
| ethylene glycol ester of montanic acid | 0,3 | 2,7 | 2600 | 2950 | 150 | 169 | 83 |
| | 0,5 | 6,3 | 2575 | 2900 | 163 | 171 | 69 |

The above results clearly show that both the $C_{30+}$ alcohols and the esters derived therefrom have the effect of an external lubricant.

EXAMPLE V

In this example the results are given of tests on a $C_{10}$ alcohol TP (derived from n-decene) and, the oleic acid ester and the diurethane thereof and diphenylmethane-4,4'-diisocyanate (MDI). TP standing for total product, i.e. the mixture of telomeric alcohols as it is obtained without the n=1 fraction having been removed. The composition was about as follows:

| | wt % |
|---|---|
| n = 1 | 30–40 |
| n = 2 | 15–20 |
| n = 3 | 20–25 |
| n = 4 | 12–15 |
| n = 5 | 8–10 |
| n ≧ 6 | 4–6 |

The formulation of the PVC used was the same as the one used in Example IV. The results are summarized in the table below. The concentration of the lubricant was in all formulations 0,5 phr.

| lubricant | Brabender gelation tests | | | | | clarity of 3 mm thick pressed sheet at 690 nm % T |
|---|---|---|---|---|---|---|
| | gelation time (min.) | fusion torque (m grams) | torque 10 min. after gelation (m grams) | temp. at fusion (°C.) | temp. after 10 min. (°C.) | |
| — | 1,2 | 2700 | 2850 | 156 | 171 | 85 |
| oleic acid ester of $TP_{10}$ alcohol | 6,4 | 2600 | 2900 | 162 | 170 | 66 |
| urethane of $TP_{10}$ alcohol and MDI | 4,1 | 2600 | 2950 | 159 | 170 | 84 |
| $TP_{10}$ alcohol glycol mono oleate | 3,0 | 2600 | 2850 | 159 | 169 | 84 |
| | 2,1 | 2600 | 2850 | 160 | 171 | 85 |
| n-butyl stearate | 2,3 | 2500 | 2850 | 158 | 171 | 85 |

EXAMPLE VI

The $C_{30+}$ alcohol prepared according to Example I and the urethane of toluene diisocyanate and the acetic acid ester, adipic acid diester and $C_{30+}$ acid ester derived therefrom were tested for their being suitable entirely or partially to replace the known Carnauba and/or montanic acid waxes. The following properties were measured.

1. Ubbelohde dropping point °C. (heating rate 1° C./min.) which is a measure of the "melting point" of the wax composition. The dropping point was determined with a Mettler FP 53 tester.
2. Ubbelohde dropping point °C. (heating rate 1° C./min.) as under 1, but after mixing 1 part of wax with 4 parts of paraffin.
3. Penetration of paraffin mixture, in accordance with ASTM D 1321-70. In this way an indication of the hardness increasing effect of the esters is obtained.
4. Continental solid point, in accordance with ASTM D 938-49. This point corresponds to the congealing point of 1 part of wax, 4 parts of paraffin and 15 parts of turpentine.
5. Consistency of paste, as described in "Vom Wachs, Hoechster Beiträge zur Kenntnis der Wachse", Farbw. Hoechst, Frankfurt-Hoechst, Vol. II, Beitrag II, p. 50–51. In that test a stamp of some particular weight and dimensions is slowly, while subjected to a gradually increasing pressure, brought into contact with the paste.
6. Solvent retention, to determine this property 1 part of the wax to be examined was mixed with 4 parts of paraffin and 15 parts of turpentine and the resulting mixture was brought into a tin. After the closed tin had been left for 17 hours at 23° C., it wasp-placed in a ventilated oven. After it had been in the oven for 7 days at 32° C. and subsequently on a table for another 7 days at 20° C., the solvent retention was measured. It is expressed as follows: solvent retention=

$$100\% - \frac{\text{amount of turpentine lost}}{\text{original amount of turpentine}} \times 100\%$$

The results are listed in the following table and compared with those of the known wax compositions or components thereof.

| Wax | dropping point | dropping[a] point of paraffin mixture (°C.) | penetration[a] of paraffin mixture (0,1 mm) |
|---|---|---|---|
| paraffin | 60 | (60) | 17 |
| carnauba prime yellow[b] | 85 | 81 | 7 |
| montanic acids | 86 | 79 | 5 |
| montanic acid ethylene glycol ester | 83 | 77 | 7 |
| montanic acid 1,3-butanediol ester-40% calcium soap | 102 | 90 | 5 |
| C30+ alcohols or the derived[d] | 88 | 73 | 10,5 |
| acetic acid ester | 81 | 68 | 14,5 |
| adipic acid diester | 90 | 74 | 9,0 |
| C30+ acid ester of C30+ alcohol | 94 | 80 | 7,5 |
| diurethane of toluene diisocyanate and C30+ alcohol | 98 | 85 | 7,5 |

[a]Paraffin mixture: 1 part of wax + 4 parts of paraffin
[b]Carnauba wax, which is a natural wax, containing 80% of esters of acids-long-chain (>C24) and substituted or unsubstituted cinnamic acid - and long-chain (>C30) alcohols.
[d]Derived from straight-chain and branched-chain C30+ alcohols according to the invention.

| Wax | paste consistency (g/cm²) | continental[c] solid point (°C.) | solvent retention (%) |
|---|---|---|---|
| Carnauba fatty gray | 1500 | 40 | 31 |
| montanic acids | 700 | 40 | 20 |
| montanic acid 1,3-butanediol ester-40% calcium soap | 765 | 40 | 51 |
| C30+ alcohols or the derived[d] | 1140 | 46 | 84 |
| acetic ester | 820 | 42 | 76 |
| adipic diester | 1170 | 43 | 82 |
| C30+ acetic ester | 950 | 45 | 63 |
| diurethane of toluene diisocyanate and C30+ alcohol | 1170 | 45 | 80 |

[c]Paste composition: 1 part of wax, 4 parts of paraffin; 15 parts of turpentine.

We claim:

1. Novel branched-chain monoalcohols having at least 20 carbon atoms and the derivatives thereof selected from the group consisting of
    (a) esters of aromatic, aliphatic or cycloaliphatic acids having at least 2 carbon atoms and 1,2 or 3 carboxyl groups;
    (b) urethanes of aromatic, aliphatic or cycloaliphatic isocyanates;
    (c) monoethers of polyalkylene oxide glycols having 2 to 50 alkylene oxide units each containing 2 or 3 carbon atoms and the alkylpolyoxyalkylene sulfates derived therefrom;
    (d) sulfates, characterized in that the structure of said branch-chain monoalcohol conforms to the formula:

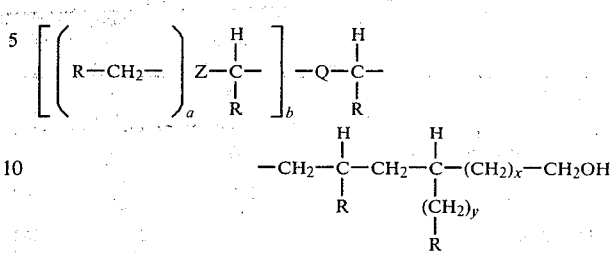

where
x is 0 or 2
and y is 0 or 2,
where
when y=2, x=0 and when y=0, x=2,
R=CH$_3$(CH$_2$)$_n$, where n represents an integer from 3 to 42;
b is 0 or 1, where
when b=0, Q represents a hydrogen atom, and when b=1, Q represents a CH$_2$-group, and
a=0 or 1, where
when a=0, z represents a hydrogen atom, and
when a=1, z represents a CH$_2$-group.

2. Novel compounds according to claim 1, characterized in that n represents an integer from 3 to 17.

3. Novel compounds according to claim 1, characterized in that n represents an integer from 17 to 42.

4. Esters according to claim 1, characterized in that the aliphatic acid is a compound having 2 to 30 carbon atoms.

5. Esters according to claim 1, characterized in that the aliphatic acid is a di- or tricarboxylic acid.

6. Esters according to claim 1, characterized in that the aliphatic acid is a dicarboxylic acid selected from the group consisting of acetylene dicarboxylic acid, fumaric acid, maleic acid or adipic acid.

7. Urethanes according to claim 1, characterized in that the aromatic isocyanate is a diisocyanate selected from the group consisting of 2,4- and/or 2,6-toluene diisocyanate and diphenylmethane-4,4'-diisocyanate.

8. Monoethers according to claim 1, characterized in that n represents an integer from 3 to 17 and that the polyalkylene oxide glycol moiety contains 2 to 15 alkylene oxide units.

9. Sulfates according to claim 1, characterized in that the sulfates are alkylpolyoxyalkylene sulfates and/or alkyl sulfates having a cation selected from the group consisting of ammonium, sodium, potassium, magnesium, diethanolamine and triethanolamine.

10. A resin composition having improved internal and external lubricant properties, comprising a polymer or copolymer of vinyl chloride and 0.1 to 5% by weight, calculated on the polymer, of said branched-chain monoalcohol and/or said derivative thereof according to the preamble of claim 1, characterized in that at least 40 percent by weight of said branched-chain monoalcohol present as such, or at least 40 percent of said derivatives thereof have a branched-chain structure, and that at least 10 percent by weight thereof correspond to the formula given in claim 1.

11. A resin composition according to claim 10, characterized in that said resin composition comprises said branched-chain monoalcohols and/or said derivatives thereof, and further comprises an alcohol and/or derivative thereof, said alcohol having the formula:

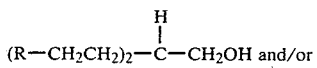 and/or

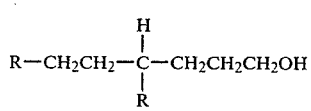

12. A resin composition according to claim 11, characterized in that said resin composition contains said branched-chain monoalcohols and or said derivatives thereof, and wherein said resin composition contains said alcohol and/or said derivatives thereof, and said composition further contains an amount of 40 to 60 percent by weight of linear aliphatic monoalcohols and/or derivatives thereof, with said linear aliphatic monoalcohol having the formula R CH$_2$CH$_2$CH$_2$CH$_2$OH, and about 30 to 40 percent by weight of γ-branched primary alcohols and/or the derivatives thereof, with said γ-branched primary alcohol having the formula:

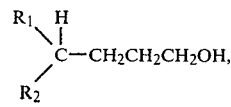

where R$_1$ and R$_2$ represent linear alkyl groups which together have the same number of carbon atoms as the group R.

13. A wax composition for entirely or partly replacing carnauba wax or montan wax and substantially consisting of one or more of said branched-chain monoalcohols and/or derivatives thereof according to the preamble of claim 1, characterized in that at least 40 percent by weight of said branched-chain monoalcohol present as such, or at least 40 percent by weight of said derivatives thereof have a branched-chain structure, and at least 10 percent by weight thereof correspond to the formula given in claim 1.

14. A wax composition according to claim 13, characterized in that said composition contains said branched-chain monoalcohols and/or said derivatives thereof and further said composition contains an alcohol and/or derivative thereof, with the alcohol having the formula:

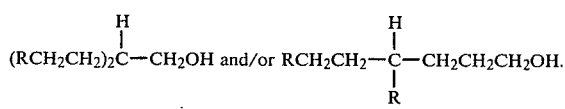

15. A wax composition according to claim 14, characterized in that said wax composition contains said branched-chain monoalcohols an amount of 40 to 60 percent by weight of linear aliphatic monoalcohols and/or derivatives thereof, with said linear aliphatic monoalcohol having the formula R CH$_2$CH$_2$CH$_2$CH$_2$OH, and about 30 to 40 percent by weight of γ-branched primary alcohols and/or derivatives thereof, with said γ-branched primary alcohol having the formula:

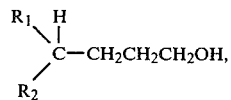

where R$_1$ and R$_2$ represent linear alkyl groups which together have the same number of carbon atoms as the group R.

* * * * *